US008999372B2

(12) United States Patent
Davidson et al.

(10) Patent No.: US 8,999,372 B2
(45) Date of Patent: Apr. 7, 2015

(54) METHODS FOR MODULATING DISSOLUTION, BIOAVAILABILITY, BIOEQUIVALENCE AND DRUG DELIVERY PROFILE OF THIN FILM DRUG DELIVERY SYSTEMS, CONTROLLED-RELEASE THIN FILM DOSAGE FORMATS, AND METHODS FOR THEIR MANUFACTURE AND USE

(75) Inventors: Robert S. Davidson, Los Angeles, CA (US); Gary Kehoe, Phoenix, AZ (US)

(73) Assignee: CURE Pharmaceutical Corporation, Oxnard, CA (US)

( * ) Notice: Subject to any disclaimer, the term of this patent is extended or adjusted under 35 U.S.C. 154(b) by 1493 days.

(21) Appl. No.: 11/371,167

(22) Filed: Mar. 7, 2006

(65) Prior Publication Data

US 2006/0210610 A1 Sep. 21, 2006

Related U.S. Application Data

(63) Continuation-in-part of application No. 10/402,273, filed on Mar. 28, 2003, now abandoned, and a continuation-in-part of application No. 10/921,770, filed on Aug. 18, 2004, and a continuation-in-part of application No. 10/713,544, filed on Nov. 14, 2003, now abandoned.

(60) Provisional application No. 60/497,186, filed on Aug. 22, 2003, provisional application No. 60/426,598, filed on Nov. 14, 2002.

(51) Int. Cl.
*A61K 47/00* (2006.01)
*A61K 9/00* (2006.01)
*A61K 9/70* (2006.01)

(52) U.S. Cl.
CPC ............. *A61K 9/0056* (2013.01); *A61K 9/7007* (2013.01)

(58) Field of Classification Search
CPC .... A61K 9/0056; A61K 9/7007; A61K 9/006
USPC ........................................................ 424/439
See application file for complete search history.

(56) References Cited

U.S. PATENT DOCUMENTS

| | | |
|---|---|---|
| 3,155,590 A | 8/1962 | Erwin et al. |
| 3,341,416 A | 12/1963 | Anderson et al. |
| 3,531,418 A | 8/1965 | Fanger et al. |
| 3,488,418 A | 11/1965 | Holliday et al. |
| 3,523,906 A | 4/1968 | Vrancken et al. |
| 3,524,910 A | 6/1969 | Holliday et al. |
| 3,703,576 A | 8/1970 | Kitajima et al. |
| 3,891,570 A | 6/1975 | Fukushima et al. |
| 3,909,444 A | 9/1975 | Anderson et al. |
| 3,931,146 A | 1/1976 | Kato et al. |
| 3,951,851 A | 4/1976 | Kitajima et al. |
| 4,072,551 A | 2/1978 | Dabal et al. |
| 4,083,741 A | 4/1978 | Goldberg |
| 4,107,072 A | 8/1978 | Morse et al. |
| 4,197,289 A * | 4/1980 | Sturzenegger et al. ........ 424/443 |
| 4,316,884 A | 2/1982 | Alam et al. |
| 4,389,330 A | 6/1983 | Tice et al. |
| 4,389,331 A | 6/1983 | Samejima et al. |
| 4,411,933 A | 10/1983 | Samejima et al. |
| 4,517,173 A | 5/1985 | Kizawa et al. |
| 4,572,833 A | 2/1986 | Pedersen et al. |
| 4,746,508 A | 5/1988 | Carey et al. |
| 4,876,092 A | 10/1989 | Mizobuchi et al. |
| 5,047,244 A | 9/1991 | Sanvordeker et al. |
| 5,055,461 A | 10/1991 | Kelleher et al. |
| 5,166,233 A | 11/1992 | Kuroya et al. |
| 5,192,552 A | 3/1993 | Fekete et al. |
| 5,196,202 A | 3/1993 | Konishi |
| 5,238,714 A | 8/1993 | Wallace et al. |
| 5,288,498 A | 2/1994 | Stanley et al. |
| 5,411,945 A | 5/1995 | Ozaki et al. |
| 5,458,890 A | 10/1995 | Williford et al. |
| 5,629,003 A | 5/1997 | Horstmann et al. |
| 5,639,469 A | 6/1997 | Benes et al. |
| 5,688,520 A | 11/1997 | Karsenty et al. |
| 5,700,478 A | 12/1997 | Biegajski et al. |
| 5,714,007 A * | 2/1998 | Pletcher et al. ............... 118/629 |
| 5,731,005 A | 3/1998 | Ottoboni et al. |
| 5,948,430 A | 9/1999 | Zerbe et al. |
| 6,010,716 A | 1/2000 | Saunal et al. |
| 6,010,718 A | 1/2000 | Al-Razzak et al. |
| 6,066,337 A | 5/2000 | Allen et al. |
| 6,139,865 A | 10/2000 | Friend et al. |
| 6,177,096 B1 | 1/2001 | Zerbe et al. |

(Continued)

FOREIGN PATENT DOCUMENTS

| | | |
|---|---|---|
| CA | 2520986 A1 | 4/2000 |
| EP | 0163924 B1 | 12/1985 |

(Continued)

OTHER PUBLICATIONS

FDA, Dissolution Testing of Immediate Release Solid Oral Dosage Forms (CDER) Aug. 1997.
FDA, Extended Release Oral Dosage Forms: Development, Evaluation, and Application of In Vitro/In Vivo Correlations (CDER) Sep. 1997.
FDA, Bioavailability and Bioequivalence Studies for Orally Administered Drug Products—General Considerations (CDER) Mar. 2003.
FDA, Clozapine Tablets: In Vivo Bioequivalence and In Vitro Dissolution Testing (CDER) Jun. 2005.
FDA, Potassium Chloride Modified-Release Tablets and Capsules: In Vivo Bioequivalence and In Vitro Dissolution Testing (CDER) Oct. 2005.

(Continued)

*Primary Examiner* — Blessing M Fubara
(74) *Attorney, Agent, or Firm* — Schwegman Lundberg & Woessner, P.A.

(57) ABSTRACT

Methods for modulating dissolution, bioavailability, bioequivalence and drug delivery profile of thin film drug delivery systems, controlled-release thin film dosage formats, and methods for their manufacture and use are disclosed.

20 Claims, No Drawings

(56) References Cited

U.S. PATENT DOCUMENTS

| | | |
|---|---|---|
| 6,284,264 B1 | 9/2001 | Zerbe et al. |
| 6,391,294 B1 | 5/2002 | Dettmar et al. |
| 6,419,903 B1 | 7/2002 | Xu et al. |
| 6,449,925 B1 | 9/2002 | Otsu et al. |
| 6,551,616 B1 | 4/2003 | Notario et al. |
| 6,596,298 B2 | 7/2003 | Leung et al. |
| 6,599,627 B2 | 7/2003 | Yeo et al. |
| 6,638,621 B2 | 10/2003 | Anderson |
| 6,660,292 B2 | 12/2003 | Zerbe et al. |
| 6,783,768 B1 | 8/2004 | Brown et al. |
| 6,872,407 B2 | 3/2005 | Notario et al. |
| 6,953,593 B2 | 10/2005 | Kuhrts |
| 6,989,195 B2 | 1/2006 | Anderson |
| 7,025,983 B2 | 4/2006 | Leung et al. |
| 7,067,116 B1 | 6/2006 | Bess et al. |
| 7,132,113 B2 | 11/2006 | Zerbe et al. |
| 7,261,939 B2 | 8/2007 | Hallett et al. |
| 8,840,919 B2 | 9/2014 | Davidson |
| 2001/0006677 A1 | 7/2001 | McGinity et al. |
| 2001/0022964 A1 | 9/2001 | Leung et al. |
| 2001/0055613 A1 | 12/2001 | Burnside et al. |
| 2002/0019447 A1 | 2/2002 | Renn et al. |
| 2002/0131990 A1 | 9/2002 | Barkalow et al. |
| 2003/0008008 A1 | 1/2003 | Leung et al. |
| 2003/0064097 A1 | 4/2003 | Patel et al. |
| 2003/0068373 A1 | 4/2003 | Luber et al. |
| 2003/0206942 A1 | 11/2003 | Kulkami et al. |
| 2003/0211136 A1 | 11/2003 | Kulkami et al. |
| 2004/0043134 A1 | 3/2004 | Corriveau et al. |
| 2004/0096569 A1 | 5/2004 | Barkalow et al. |
| 2004/0131662 A1 | 7/2004 | Davidson |
| 2004/0136922 A1 | 7/2004 | Leung et al. |
| 2004/0136923 A1 | 7/2004 | Davidson |
| 2004/0191302 A1 | 9/2004 | Davidson |
| 2004/0202698 A1 | 10/2004 | Ramji et al. |
| 2004/0247646 A1 | 12/2004 | Ivory et al. |
| 2004/0247647 A1 | 12/2004 | Ivory et al. |
| 2004/0247648 A1 | 12/2004 | Fadden et al. |
| 2004/0247649 A1 | 12/2004 | Pearce et al. |
| 2005/0003048 A1 | 1/2005 | Pearce et al. |
| 2005/0031675 A1 | 2/2005 | Leung et al. |
| 2005/0089548 A1 | 4/2005 | Virgalitto et al. |
| 2005/0136096 A1 | 6/2005 | Davidson |
| 2006/0039953 A1 | 2/2006 | Leung et al. |
| 2006/0147493 A1 | 7/2006 | Yang et al. |
| 2006/0205629 A1 | 9/2006 | MacQuarrie |
| 2006/0210610 A1 | 9/2006 | Davidson et al. |
| 2007/0087036 A1 | 4/2007 | Durschlag et al. |
| 2007/0122455 A1 | 5/2007 | Myers et al. |
| 2009/0023087 A1* | 1/2009 | Kim et al. ............... 430/109.3 |
| 2009/0155701 A1* | 6/2009 | Kim et al. ............... 430/48 |

FOREIGN PATENT DOCUMENTS

| | | | |
|---|---|---|---|
| EP | 0262422 A | | 4/1988 |
| FR | 2071223 | | 9/1971 |
| RU | 2065302 C1 | | 8/1996 |
| WO | WO 94/14331 | | 7/1994 |
| WO | WO 95/34286 | | 12/1995 |
| WO | WO 97/05786 | | 2/1997 |
| WO | WO 98/20861 | * | 5/1998 |
| WO | WO 98/20863 | | 5/1998 |
| WO | WO 99/17753 | | 4/1999 |
| WO | WO 00/18365 | | 4/2000 |
| WO | WO 00/59423 | * | 10/2000 |
| WO | WO 01/35934 | | 5/2001 |
| WO | WO 01/70194 | | 9/2001 |
| WO | WO 02/02085 | | 1/2002 |
| WO | WO 02/02126 | | 1/2002 |
| WO | WO 03/015748 | | 2/2003 |
| WO | WO 2004/087089 | | 10/2004 |

OTHER PUBLICATIONS

J.R. Nixon (Editor), Microencapsulation, (1976) Contents (vii-ix); Ch. 7 (93-101); Ch. 10 (119-128); Ch. 11 (129-138); Ch. 13 (143-162); Ch. 16 (185-192); CH. 17 (193-206).

Bechtel, W. Radiology 161, 601-604 (1986).

Skelly, J. P., et al., "Workshop Report: Scaleup of Oral Extended-Release Dosage Forms," Pharmaceutical Research, 10(12): 1800-1805, 1993.

Blume, et al., Pharmaceutical Research, 10:1806-1811 (1993).

Database WPI, Section Ch, Week 200375, Derwent Publications Ltd., London, GB; XP-002322049 & KR 2003 054221 A (AEKYUNG IND CO LTO) Jul. 2, 2003 (Abstract).

U.S. Patent and Trademark Office; Internatinal Search Report and Written Opinion for International Application No. PCT/US06/08243, mailed Nov. 9, 2006.

U.S. Patent and Trademark Office—International Search Report and Written Opinion for International Application No. PCT/US08/80362, mailed Dec. 22, 2008.

*Ranbaxy* v. *Abbott*, Nos. 04 C 8078 & 05 C 1490, Nov. 10, 2005 Memorandum Opinion and Order.

"", Patent Abstracts of Japan, vol. 015, No. 398 and JP 03164139A (Abstract), (Oct. 9, 1991).

"U.S. Appl. No. 10/402,273, Examiner Interview Summary mailed Apr. 11, 2007", 3 pgs.

"U.S. Appl. No. 10/402,273, Examiner Interview Summary mailed Jun. 18, 2008", 2 pgs.

"U.S. Appl. No. 10/402,273, Examiner Interview Summary mailed Aug. 4, 2006", 3 pgs.

"U.S. Appl. No. 10/402,273, Final Office Action mailed Nov. 26, 2008", 16 pgs.

"U.S. Appl. No. 10/402,273, Final Office Action mailed Nov. 27, 2006", 9 pgs.

"U.S. Appl. No. 10/402,273, Non Final Office Action mailed Feb. 8, 2008", 11 pgs.

"U.S. Appl. No. 10/402,273, Non Final Office Action mailed Feb. 27, 2008", 11 pgs.

"U.S. Appl. No. 10/402,273, Non Final Office Action mailed Mar. 16, 2006", 6 pgs.

"U.S. Appl. No. 10/402,273, Response filed May 25, 2007 to Final Office Action mailed Nov. 27, 2006", 11 pgs.

"U.S. Appl. No. 10/402,273, Response filed Aug. 8, 2008 to Non Final Office Action mailed Feb. 8, 2008", 13 pgs.

"U.S. Appl. No. 10/402,273, Response filed Aug. 16, 2006 to Non Final Office Action mailed Mar. 16, 2006", 17 pgs.

"U.S. Appl. No. 10/402,273, Response filed Nov. 5, 2007 to Restriction Requirement mailed Aug. 10, 2007", 9 pgs.

"U.S. Appl. No. 10/402,273, Restriction Requirement mailed Aug. 10, 2007", 5 pgs.

"U.S. Appl. No. 10/713,544, Final Office Action mailed Mar. 17, 2010", 14 pgs.

"U.S. Appl. No. 10/713,544, Final Office Action mailed Jun. 25, 2008", 9 pgs.

"U.S. Appl. No. 10/713,544, Non Final Office Action mailed May 12, 2009", 9 pgs.

"U.S. Appl. No. 10/713,544, Non Final Office Action mailed Nov. 9, 2007", 10 pgs.

"U.S. Appl. No. 10/713,544, Response filed Feb. 25, 2008 to Non Final Office Action mailed Nov. 9, 2007", 12 pgs.

"U.S. Appl. No. 10/713,544, Response filed Aug. 2, 2007 to Restriction Requirement mailed Apr. 2, 2007", 3 pgs.

"U.S. Appl. No. 10/713,544, Response filed Nov. 12, 2009 to Non Final Office Action mailed May 12, 2009", 15 pgs.

"U.S. Appl. No. 10/713,544, Response filed Dec. 24, 2008 to Final Office Action mailed Jun. 25, 2008", 13 pgs.

"U.S. Appl. No. 10/713,544, Restriction Requirement mailed Apr. 2, 2007", 9 pgs.

"U.S. Appl. No. 10/921,770, Final Office Action mailed Feb. 2, 2010", 14 pgs.

"U.S. Appl. No. 10/921,770, Final Office Action mailed Jun. 24, 2008", 10 pgs.

"U.S. Appl. No. 10/921,770, Non Final Office Action mailed Mar. 12, 2009", 13 pgs.

(56) References Cited

OTHER PUBLICATIONS

"U.S. Appl. No. 10/921,770, Non Final Office Action mailed May 29, 2014", 7 pgs.
"U.S. Appl. No. 10/921,770, Non Final Office Action mailed Jul. 12, 2011", 14 pgs.
"U.S. Appl. No. 10/921,770, Non Final Office Action mailed Sep. 18, 2007", 17 pgs.
"U.S. Appl. No. 10/921,770, Response filed Jan. 13, 2014 to Non Final Office Action mailed Jul. 12, 2011", 24 pgs.
"U.S. Appl. No. 10/921,770, Response filed Mar. 18, 2008 to Non Final Office Action mailed Sep. 18, 2007", 30 pgs.
"U.S. Appl. No. 10/921,770, Response filed Aug. 2, 2010 to Final Office Action mailed Feb. 2, 2010", 26 pgs.
"U.S. Appl. No. 10/921,770, Response filed Sep. 14, 2009 to Non Final Office Action mailed Mar. 12, 2009", 29 pgs.
"U.S. Appl. No. 10/921,770, Response filed Dec. 24, 2008 to Final Office Action mailed Jun. 24, 2008", 30 pgs.
"U.S. Appl. No. 10/921,770, Restriction Requirement mailed Aug. 10, 2007", 13 pgs.
"U.S. Appl. No. 11/836,758, Final Office Action mailed Feb. 21, 2014", 10 pgs.
"U.S. Appl. No. 11/836,758, Non Final Office Action mailed Jun. 27, 2011", 9 pgs.
"U.S. Appl. No. 11/836,758, Notice of Allowance mailed May 16, 2014", 8 pgs.
"U.S. Appl. No. 11/836,758, Response filed Apr. 23, 2014 to Final Office Action mailed Feb. 21, 2014", 9 pgs.
"U.S. Appl. No. 11/836,758, Response filed Dec. 25, 2013 to Non Final Office Action mailed Jun. 27, 2013", 9 pgs.
"European Application Serial No. 03786775.1, Supplementary European Search Report mailed Oct. 26, 2007", 5 pgs.
"European Application Serial No. 04781769.7, Supplementary European Search Report mailed Jun. 20, 2008", 6 pgs.
Blachford, "Metallic Stearates", [Online]. Retrieved from Internet: <http://blachford.ca/stearates-metallic.php>, (Jun. 4, 2011).
Yasuhide, et al., "Saccharides for the Treatment of Respiratory Tract Diseases", Database CA Online No. XP-002346984, Chemical Abstracts Service, Columbus, Ohio, Ueshima Database Accession No. 132:146641 and JP2000044488A2, 2 pgs, 2000.
"U.S. Appl. No. 10/921,770, Response filed Aug. 29, 2014 to Non Final Office Action mailed May 29, 2014", 21 pgs.
"U.S. Appl. No. 14/490,959, Preliminary Amendment filed Sep. 22, 2014", 7 pgs.

\* cited by examiner

METHODS FOR MODULATING DISSOLUTION, BIOAVAILABILITY, BIOEQUIVALENCE AND DRUG DELIVERY PROFILE OF THIN FILM DRUG DELIVERY SYSTEMS, CONTROLLED-RELEASE THIN FILM DOSAGE FORMATS, AND METHODS FOR THEIR MANUFACTURE AND USE

PRIORITY CLAIM

This application is a continuation-in-part of U.S. application Ser. No. 10/402,273 filed Mar. 28, 2003 now abandoned; this application is also a continuation-in-part of U.S. application Ser. No. 10/921,770, filed Aug. 18, 2004, which application Ser. No. 10/921,770 claims priority from U.S. Provisional Application Ser. No. 60/497,186, filed Aug. 22, 2003; this application is also a continuation-in-part of U.S. application Ser. No. 10/713,544 filed on Nov. 14, 2003 now abandoned, which application Ser. No. 10/713,544 claims priority from U.S. Provisional Application Ser. No. 60/426,598, filed Nov. 14, 2002. All the above referenced applications and provisional applications are incorporated herein by reference as if fully set forth herein in their entirety, including all drawings, figures and examples.

FIELD OF THE INVENTION

This invention relates to delivery of drugs, nutrients and other compounds to a biological organism. Thin film dosage formats, including bi-layer film dosage formats, containing controlled-release formulations are disclosed.

BACKGROUND OF THE INVENTION

Thin film dosage formats are known in the art. One of the often cited advantages of thin film dosage formats is the rapid dissolution of the thin film. This rapid dissolution provides for the immediate availability of an active ingredient in the thin film. Although this rapid availability characteristic of thin films can be very useful, it also entails certain disadvantages.

The absorption of an active ingredient after oral administration depends on several variables, including the release of the active ingredient from the dosage format, the dissolution or solubilization of the active ingredient under physiological conditions, and the permeability of the active ingredient across the oral mucosa and gastrointestinal tract.

New drug applications (NDAs) submitted in the United States to the Food and Drug Administration (FDA) contain bioavailability data and in vitro dissolution data, that, together with chemistry, manufacturing, and controls data, characterize the quality and performance of the drug product. This information for approved drugs can be found in FDA's *Approved Drug Products with Therapeutic Equivalence Evaluations* (Orange Book). Once the specifications are established in an NDA, the dissolution specifications for batch-to-batch quality assurance are generally also published in the United States Pharmacopeia (USP) as compendial standards, which generally become the official specifications for all subsequent products with the same active ingredients.

Acceptable bioequivalence data and comparable in vitro dissolution and chemistry, manufacturing, and controls data are required for approval of abbreviated new drug applications (ANDAs) (21 CFR 314.94) in the United States. Regulations at 21 CFR part 320 address the requirements for bioavailability and bioequivalence data for approval of drug applications and supplemental applications.

Accordingly, it would be highly desirable to provide an improved edible film, and processes for making the same, that permitted modulating the dissolution, plasma peak height, bioavailability and/or bioequivalence of an active ingredient delivered in an oral thin film format such as to facilitate meeting compendial values for reference products in the United States, and their equivalent in other countries. It would also be desirable to provide time release dosage formats and methods that reduce the necessity of administering therapeutic compounds, drugs and other agents invasively (e.g., such as by injection) and that permit the delivery of medicants at a specific rate over time by oral administration. These and other advantages of the present invention are disclosed herein.

SUMMARY OF THE INVENTION

In a first, separate aspect of the present invention, a composition for the oral administration of an active ingredient includes a film layer and an applied coating. The film layer is made from a composition having an effective dissolution rate in the oral cavity. The applied coating includes a powder matrix having one or more active ingredients.

In a second, separate aspect of the present invention, a composition for the oral administration of an active ingredient includes a film layer and an applied coating. The film layer is made from a composition having an effective dissolution rate in the oral cavity. The applied coating includes one or more controlled-release active ingredients.

In a third, separate aspect of the present invention, an edible film for delivering a controlled-release active ingredient formulation via the oral cavity includes an edible film having one or more controlled-release active ingredients.

In a fourth, separate aspect of the present invention, a method of administering an active ingredient to an individual includes the steps of (a) providing an edible film in accordance with the present invention (b) applying the edible film to a mucous membrane of the individual.

In a fifth, separate aspect of the present invention, a method of making a composition for the oral administration of an active ingredient includes (a) forming an edible film; (b) applying a coating to said edible film; wherein the coating includes a powder matrix having one or more active ingredients.

In a sixth, separate aspect of the present invention, a method of making a composition for the oral administration of a controlled-release active ingredient includes (a) forming an edible film; (b) applying a coating to said edible film; wherein the coating includes a controlled-release active ingredient.

In a seventh, separate aspect of the present invention, a method of making a composition for the oral administration of a controlled-release active ingredient includes forming an edible film wherein the edible film includes a controlled-release active ingredient.

Other aspects of the invention are described and will become apparent from the following detailed description of the preferred embodiments.

DETAILED DESCRIPTION OF THE PREFERRED EMBODIMENTS

In order to fully understand the manner in which the above-recited details and other advantages and objects according to the invention are obtained, a more detailed description of the invention will be rendered by reference to specific embodiments thereof.

The film dosage formats of the present invention provide an inexpensive, convenient and immediate method for delivery of a medicament without the undesirable aspects associated with certain oral or nasal delivery methods, while providing versatility, safety and patient comfort.

In one embodiment, the present invention relates to delivery of drugs, nutrients and other compounds to a biological organism. Thin film dosage formats, including bi-layer film dosage formats, containing controlled-release formulations are disclosed. Thin film compositions containing controlled-release or micro-encapsulated drugs, nutrients and other compounds in accordance with the present invention find use, inter alia, in meeting regulatory dissolution, bioavailability and bioequivalency requirements or for a time-release delivery effect of an active ingredient to an organism. The invention further provides methods for processing microencapsulated active ingredients into a bi-layer thin film. The invention further pertains to edible films for controlled-release delivery of medicaments for treatment or prevention of disease or symptom associated with a disease or disorder.

A drug delivery system according to the present invention includes an edible film. In one embodiment, an edible film in accordance with the present invention includes a controlled-release active ingredient. The edible film dissolves in the oral cavity of a user thereby delivering an appropriate dosage of the controlled-release active ingredient to the user.

In accordance with an embodiment of the present invention a controlled-release thin film dosage format includes a controlled-release active ingredient on a carrier, wherein the carrier is an edible "thin film" or "strip."

In accordance with another embodiment of the present invention a controlled-release thin film dosage format includes a controlled-release active ingredient within a carrier, wherein the carrier is an edible "thin film" or "strip."

Any effective edible "thin film" or "strip" may be used in accordance with the present invention. Unless otherwise specified or required by the context, the edible films of the present invention may be manufactured in any effective manner. U.S. Patent Application Nos. 20010022964, 20020131990, 20020019447, 20040096569, 20040191302 and U.S. Pat. Nos. 6,419,903, 3,931,146, 5,411,945, 6,010,716, 5,629,003, 5,948,430, 6,177,096, 6,284,264, 5,700,478, 6,449,925, 4,072,551, 4,083,741, all of which are incorporated herein by reference as if fully set forth herein, describe methods for making edible films. These, and other methods known in the art, or described herein, may be used in accordance with the present invention.

In one embodiment, an edible film according to the present invention comprises a bi-layer film which generally includes a first layer that is generally water soluble and that generally serves as a substrate layer and a second layer that is generally in the form of a powder, powder matrix, dry coat, or the like. The dry coat layer may generally be applied after partial curing of the substrate layer, affixing itself to this substrate layer. See, e.g., United States Patent Application 20040191302. While in accordance with this embodiment of the invention one or more active ingredients may be contained in either layer, preferably the dry coat layer will contain one or more active ingredients. Said dry coat layer and similar layers are especially effective with low dose active ingredients that require a very low moisture environment to remain stable.

The dry coat layer may include any effective ingredients. In one embodiment, the dry coal layer includes substrates, and the like. In another embodiment, the dry coat layer includes partitioning agents, and the like.

A film in accordance with the present invention is generally of a size adapted such that the film is fast dissolving. The weight per strip may vary depending on the application. Generally, the strip may have any effective weight. For human consumption, for example, certain effective weights of the strip include from about 10 to about 400 mg, about 20 to about 200 mg, about 30 to about 100 mg and about 50 mg.

Any effective dosing may be provided per strip. The maximum dosing per strip will generally vary depending on the choice of active ingredient and the weight of the strip. In a 100 mg strip for human consumption, the active ingredient may generally be present in a range from about 0.01 to about 50 mg, about 0.1 to about 25 mg, about 1 to about 20 mg and about 12.5 mg.

Active ingredients can be delivered in any effective state, including in a solid format, liquid format, or other format, including, for example, gels and pastes. Depending on dose levels, the active ingredients generally can be oil or water soluble. Generally, active ingredients that are stable in aqueous systems are preferred. Active ingredients that are not stable in an aqueous system, however, though not preferred, may still be used. Preferably, the dosage per serving is 1-2 strips but may vary depending on the size of the individual strip and other factors known to one skilled in the art.

Individual strips can be made in virtually any size. When intended for human consumption, the strips generally are $^{13}/_{16}$ inch by 1 ¼ inch rectangles, and the thickness of the first layer is generally in a range between about 0.040 to 1.1 micrometers. The thickness of the second dry coat layer is generally in the range of about 0.007 to 0.02 micrometers. The thickness of the particularly layers may be more or less than the values recited herein depending on factors known to one skilled in the art such as load and processing challenges.

Any standard manufacturing procedure known in the art may be used to manufacture a film in accordance with the present invention. An example of such a process can be found in U.S. Pat. No. 5,948,430 to ZERBE et al.

Further to the production method described in U.S. Pat. No. 5,948,430 to ZERBE et al., the production of a film according to the present invention can also include an aeration step. This step includes aerating the mass prior to application onto a substrate. Aeration is most preferably achieved through mechanical agitation, mechanical reaction, or carbon dioxide aeration. The aeration step produces a film having greater thickness and lower density than without aeration.

A further embodiment of the present invention includes an improved film and method for making the same. The film can be used on living cells. Formation of the medicant-containing layer in the film does not require a solvent and minimizes the likelihood of damage from heat and shear. The rate of dissolution or delivery of the medicant by the film can be readily adjusted. The medicant-containing layer, while minimizing the likelihood of heat induced medicant damage, permits heat to be utilized to form a coating on the edible film. Hydrophilic components can be readily incorporated in larger concentrations during production of the medicant-containing layer.

Further, the present invention includes an improved composition for delivering a medicant in the oral cavity. The composition includes an applied coating and a film layer.

An edible film in accordance with the present invention may be made from any effective polymer, softener, filler, matrix, or other composition. The film has an acceptable dissolution rate in the oral cavity for a particular thickness of film. For example, if the film has a thickness of 50 microns, it may be desirable for the film to dissolve in the oral cavity within about fifteen seconds. Or it may be desirable for the film to dissolve more slowly. By way of example, and not limitation, the film can be made with pullulan, modified starch, pectin, carageenan, a maltrodextrin, or alginate.

By way of example, and not limitation, the film layer can be produced using a highly water-soluble polymer comprising a natural or synthetic water-soluble polymer. The polymer preferably has good film moldability, produces a soft flexible film, and is safe for human consumption. One such polymer can be a water-soluble cellulose derivative like hydroxypropyl cellulose (HPC), methyl cellulose, hydroxypropyl alkylcellulose, carboxymethyl cellulose or the salt of carboxymethyl cellulose. Or, the polymer can comprise an acrylic acid copolymer or its sodium, potassium or ammonium salt. The acrylic acid copolymer or its salt can be combined with methacrylic acid, styrene or vinyl type of ether as a comonomer, poly vinyl alcohol, poly vinyl pyrrolidone, polyalkylene blycol, hydroxy propyl starch, alginic acid or its salt, poly-saccharide or its derivatives such as trangacanth, bum gelatin, collagen, denatured gelatin, and collagen treated with succinic acid or anhydrous phthalic acid. By way of example, the following can be included in the powder matrix as adhesives: poorly water-soluble cellulose derivatives including ethyl cellulose, cellulose acetate and butyl cellulose; shellac; higher fatty acids including steric acid and palmitic acid. The following can also, without limitation, be used to produce the film layer: pullulan, maltodextrin, pectin, alginates, carrageenan, guar gum, other gelatins, etc.

The-thickness of the film layer can vary as desired, but typically is in the range of 0.01 mm to 3.00 mm, preferably 0.03 mm to 1.00 mm.

The applied coating in accordance with the present invention may be made from any effective composition. In one embodiment the applied coating is a powder matrix including one or more medicants or active ingredients. In one embodiment of the present invention the medicant or active ingredient is provided in a controlled-release format. The medicant or active ingredient can be contained in a powder carrier, or can itself be a powder. The powder matrix is normally applied to the film layer to form a coating after the film layer has been manufactured.

Applying an active ingredient as a powder matrix ordinarily does not require the use of a solvent and the powder matrix may include, in addition to the medicant or active ingredient, a variety of different auxiliary compositions.

The powder matrix can be admixed in a fluidized bed, minimizing the generation of shear and heat. In a fluidized bed dry air or another gas is dispersed upwardly through a plurality of openings to suspend and intermix particulate. Any desired means can be used to admix powders. Another advantage of mixing or suspending powder in a fluidized bed is that the dry air suspending the powder particles tends to prevent agglomeration of the particles. The admixed powder matrix can also be stored (i.e., suspended) in the fluidized bed, prior to the application of the admixed powder matrix to the film layer. The powder matrix can be applied in any desired manner, including sifting, screening, atomization, static, mechanical agitation, etc. For example, the powder matrix can be atomized through a Nordson or similar static spray gun using compressed air. One such gun creates a fine mist spray of powder particles. The gun statically electrically charges the powder particles so they adhere to a surface of the film layer that is receiving the powder particles. Another process for applying the powder particles is to admix the particles with a liquid carrier to form a particle-liquid solution. The particle-liquid solution is sprayed on the film layer. The liquid carrier evaporates, leaving the powder particles on the film. The liquid carrier preferably does not cause the powder particles to dissolve in the liquid carrier.

One auxiliary composition that can be included in the powder matrix with the medicant is a composition that dissolves slowly over a selected period of time. Such an auxiliary dissolution control composition can be utilized to slow the release of medicant in the oral cavity. Examples of this kind of auxiliary composition are, without limitation, gel forming compositions like carrageenan, gelatin, alginates, pullulan, PVP, and other hydrophilic materials; cyclodextrin; and, inert materials like calcium and fibers. For example, the fibers can comprise carboxymethylcellulose.

Another auxiliary composition the can be included in the powder matrix with the medicant is an absorption composition that absorbs water or saliva. Such an auxiliary absorption composition can be also be used to slow the release of medicant, and/or, to form a gel. The gel can, if desired, cause the strip to become chewable, similar to a very soft jelly-bean. As used herein, an auxiliary composition is termed a gel if, when it is placed in the oral cavity or in contact with another source of bodily liquid, (1) the auxiliary composition absorbs at least four times it weight of water or of saliva or other aqueous solution in a selected period of time, or (2) the auxiliary composition swells to at least three times its thickness in a selected period of time. The selected period of time can vary but preferably is from five seconds to fifteen minutes, most preferably five seconds to five minutes. Examples of gel auxiliary compositions include, without limitation, carboxymethylcellulose, pectin, modified starches, gelatin, and carrageenan. These compositions can be used alone or in combination. One advantage of a gel is that it tends to slow the dissolution of the medicant in the oral cavity and to maintain the medicant in the oral cavity for a longer period of time.

A further auxiliary composition that can be included in the powder matrix is a composition that, when placed in the oral cavity in contact with the mucosa therein, adheres to the mucosa. The concentration of such auxiliary adhesion compositions in the powder matrix can be adjusted to vary the length of time that the film adheres to the mucosa or to vary the adhesive forces generated between the film and mucosa. The auxiliary adhesion compositions adhere to the oral mucosa or to mucosa or tissue in other parts of the body, including the mouth, nose, eyes, vagina, and rectum. Examples of auxiliary adhesion compositions include carboxymethycellulose, polyvinyl alcohol, polyvinyl pyrrolidone (povidone), sodiumalginate, methyl cellulose, hydroxyl propyl cellulose, hydroxypropylmethyl cellulose, polyethylene glycols, carbopol, polycarbophil, carboxyvinyl copolymers, propylene glycol alginate, alginic acid, methyl methacrylate copolymers, tragacanth gum, guar gum, karaya gum, ethylene vinyl cetate, dimenthylpolysiloxanes, polyoxyalkylene block copolymers, and hydroxyethylmethacrylate copolymers. All examples of composition provided herein are given without limiting the use or inclusion of other comparable or finctionally equivalent compositions even though such comparable or functionally equivalent compositions are not listed.

Still another auxiliary composition that can be included in the powder matrix is a flow composition that, when subjected to a curing process, flows to form a smoother or shinier coating on the exterior of the film layer. One preferred curing process is heating the film layer with powder coating to a selected temperature above 76 degrees F. to cause the auxiliary flow composition to soften and flow. Examples of this kind of auxiliary composition are lipids (including various animal and vegetable fats) waxes, particularly low melting point waxes, and polyols, particularly low melting point polyols that can be admixed in powder form or than can included be in powder particles containing a medicant or other compositions. The medicant itself, may also have the property of flowing at an elevated temperature in excess of 76 degrees F. to form a smoother or shinier coating.

Other auxiliary compositions that can be included in the powder matrix include, without limitation, bulking agents, fillers, pigments (coloring), flavorings, scents, and sweeteners.

Combinations of auxiliary compositions can be included in the powder matrix to achieve a desired function. For example, if it is desired to slow the dissolution of a medicant in the oral cavity, less soluble fillers and fibers can be included in the powder matrix along with a high concentration of polymers that have a very high degree of ability to adhere to the oral mucosa lining the mouth.

The dry powder matrix will normally contain a minor amount of retained or bound water or other liquid, typically less than about ten percent by weight. The level of moisture in the powder matrix normally should not cause the powder particles to stick or adhere to one another during intermixing of powders to form the powder matrix and during application of the powder matrix to the film layer.

Bulking agents that can be included in the powder matrix include, by way of example and not limitation, avicel, sugar alchohols including manitol and sorbitol and xylitol and isomalt, lactic sugar, sorbitol dextrin, starch, anhydrous calcium phosphate, calcium carbonate, magnesium trisilicate, silica, and amylase.

The size of particulate in the powder matrix can vary as desired, but is preferably in the range of 10 mesh to 400 mesh or finer, preferably 40 mesh to 300 mesh.

The powder matrix can be applied to one or both sides of the film layer. The film layer includes upper outer surface on the top of the film layer and includes a lower outer surface on the bottom of the film. The upper outer surface is generally parallel to the lower outer surface. The top of the film is generally parallel to the bottom of the film. The thickness of the powder matrix layer can vary as desired, but is preferably in the range of 0.001 mm to 3.00 mm, preferably 0.01 mm to 1.00 mm.

If desired, after the powder matrix layer is applied to the film layer, an additional layer or layers can be applied over the powder matrix layer to seal the powder matrix layer, slow the dissolution of the medicant from the powder matrix layer, or obtain other desirable results.

If desired, multiple powder matrix layers can be applied to a film layer. A film layer can comprise a laminate of two or more layers. Methods for producing the film layer and incorporating plasticizers, bulking agents, taste modifying agents, pigments, etc. in the film layer are well known in the art and not described in detail herein. Since the medicant may be applied to the film layer in a dry powder form, the likelihood of adverse interactions between the medicant and compositions comprising the film layer is lessened.

Unless otherwise specified or required by the context, the term edible as used herein is used interchangeably with the term orally consumable, and generally means that the article may be placed in the mouth, oral cavity, on the tongue, or the like, without significant detrimental effect to the recipient.

In certain embodiments the compositions and films of the present invention may contain at least one flavoring and/or odorant composition that renders the composition or film more palatable. Any effective flavor or odor may be used. The flavoring or odor agent or agents may be present in any effective amount, including, for example, in an amount ranging from about 0.5 to 40 wt. %, 1 to 30 wt. %, 5 to 15 wt. %, 0.5 to 15 wt. %. The flavorings may be natural or artificial, or combinations thereof. See, e.g., U.S. Pat. No. 5,458,890, which is incorporated herein by reference. In one embodiment of the present invention a flavoring or odor agent or agents is present in the film layer. In another embodiment of the present invention a flavoring or odor agent or agents is present in the powder matrix layer. In yet another embodiment of the present invention a flavoring or odor agent or agents is present in the film layer and the powder matrix layer.

Generally, active ingredients in the un-ionized form are more readily transported across the mucosal membrane. Therefore, in accordance with one embodiment, the edible film of the present invention includes an agent for adjusting pH conditions to either maximize or minimize the percentage of un-ionized active ingredient available in the oral cavity, such as to modulate the rate of mucosal absorption of active ingredient. Buffering agents are particularly important for those active ingredient that partially ionize within the pH range of the mouth, such as weak acid and weak base drugs. Generally, buffering agents are more important when hydrophilic active ingredient are used because those drugs usually have lower mucosal permeability and dissolve more readily in saliva within the mouth. In one embodiment, the film layer includes one or more buffer forming agents, pH control agents, or both. In another embodiment, the powder matrix layer includes one or more buffer forming agents, pH control agents, or both. In yet another embodiment, both layers include one or more buffer forming agents, pH control agents, or both.

Generally, permeation enhancers improve the permeability of active ingredients at the mucosal membrane. Therefore, in accordance with one embodiment, the edible film of the present invention includes one or more permeation enhancers to modulate the rate of mucosal absorption of active ingredient. In one embodiment, the film layer includes one or more permeation enhancers. In another embodiment, the powder layer includes one or more permeation enhancers. In yet another embodiment, both layers include one or more permeation enhancers. In accordance with another embodiment of the present invention, the permeability of both lipophilic and nonlipophilic drugs may be improved by using suitable permeation enhancers.

Any effective permeation enhancers may be used in accordance with the present invention. An effective permeation enhancer will depend on several variables, including the active ingredient and the effect desired. Generally used permeation enhancers include bile salts such as sodium cholate, sodium glycocholate, sodium glycodeoxycholate, taurodeoxycholate, sodium deoxycholate, sodium lithocholate chenocholate, chenodeoxycholate, ursocholate, ursodeoxycholate, hyodeoxycholate, dehydrocholate, glycochenocholate, taurochenocholate, and taurochenodeoxycholate. Other permeation enhancers such as sodium dodecyl sulfate ("SDS"), dimethyl sulfoxide ("DMSO"), sodium lauryl sulfate, salts and other derivatives of saturated and unsaturated fatty acids, surfactants, bile salt analogs, derivatives of bile salts, or such synthetic permeation enhancers as described in U.S. Pat. No. 4,746,508, which is hereby incorporated by reference as if fully set forth herein, may also be used.

In certain embodiments the compositions and films of the present invention may contain at least one ingredient or agent that is pharmaceutically active. Any effective pharmaceutically active ingredient or agent may be used in accordance with the present invention. The pharmaceutically active ingredient or agent may be present in any effective amount, including, for example, in an amount ranging from about 0.5 to 40 wt. %, 1 to 30 wt. %, 5 to 15 wt. %, 0.5 to 15 wt. %. In one embodiment, a film layer in accordance with the present invention includes one or more active ingredients. In another embodiment, a powder matrix layer in accordance with the present invention includes one or more active ingredients. In yet another embodiment, a film layer in accordance with the present invention and a powder matrix layer in accordance with the present invention include one or more active ingredients.

In accordance with an embodiment of the present invention an active ingredient may be formulated in a controlled-release format. The active ingredient may be formulated in a controlled-release format in any effective manner. In one embodiment, controlled-release of an active ingredient is obtained by microencapsulation, or the like.

In accordance with an embodiment of the present invention, one or more active ingredients in accordance with the present invention are provided in a controlled release dosage form. A controlled release dosage form in accordance with the present invention is a dosage form wherein the active ingredient release characteristics of the dosage form provide for a time course and/or location that are chosen to accomplish therapeutic or convenience objectives not offered by conventional dosage forms such as a solution or an immediate release dosage form. Controlled-release dosage forms include, for example fast-, medium-, slow, delayed-, and extended-release.

In one embodiment, one or more active ingredients in accordance with the present invention are provided in a delayed release form. In accordance with the present invention, delayed release forms provide for the release of one or more active ingredients at a time other than immediately following oral administration.

In one embodiment, one or more active ingredients in accordance with the present invention are provided in a delayed release form including an enteric coating. In accordance with the present invention, enteric coated forms provide for the release of one or more active ingredients after the dosage form has passed through the stomach.

In one embodiment, one or more active ingredients in accordance with the present invention are provided in a fast release form. In accordance with the present invention, a fast release form provides for the release of one or more active ingredients after the active has been swallowed but before it has passed through the stomach.

In one embodiment, one or more active ingredients in accordance with the present invention are provided in an extended release form. In accordance with the present invention, extended release forms make the active ingredient available over an extended period after ingestion (for example, between about 2 and about 48 hours, between about 4 and about 24 hours, between about 10 and about 16 hours), by, for example, affecting the dissolution, absorption, or the like, of one or more active ingredients. This generally allows a reduction in dosing frequency compared to a drug presented as a conventional dosage form (e.g., as a solution or an immediate release dosage form).

In one embodiment, one or more active ingredients in accordance with the present invention are provided in an immediate release form. In accordance with the present invention, immediate release forms make the active ingredient available after dissolution of the film dosage format without delaying or prolonging the dissolution or absorption of the active ingredient.

In yet another embodiment, an edible film in accordance with the present invention includes an effective mixture of the different controlled-release and/or immediate release (e.g., non-encapsulated) forms such as to obtain a desired dissolution, bioavailability and/or bioequivalence profile for one or more active ingredients.

In one embodiment, the film layer includes one or more controlled-release active ingredients. In another embodiment, the powder matrix layer includes one or more controlled-release active ingredients. In yet another embodiment, both layers include one or more controlled-release active ingredients.

In accordance with an embodiment of the present invention, a controlled-release thin film dosage format includes a film of the present invention having an active ingredient formulation comprising a multiplicity (typically at least 10) of individual coated (e.g., "microencapsulated") units such that the individual units will be made available from the formulation upon disintegration of the formulation in the mouth of animals, including humans, who have an edible film of the present invention placed in their oral cavity. In one embodiment, the film layer includes a multiplicity of individual coated units. In another embodiment, the powder matrix layer includes a multiplicity of individual coated units. In yet another embodiment, both layers include a multiplicity of individual coated units.

In one embodiment the present invention provides an edible film which disintegrates in the mouth to make available a multiplicity of individual controlled-release units contained in the edible film. In one embodiment, the active ingredient is made available in the gastrointestinal tract as the individual swallows the controlled-release units. In another embodiment, the active ingredient is made available in the oral cavity for absorbtion via the oral mucosa as the active ingredient is released from the controlled-release units while they are still in the mouth. In other embodiments, combinations of controlled-release units are included in the edible film. In yet other embodiments, combinations of controlled-release units and immediate-release active ingredient are included in the edible film.

When controlled release in accordance with the present invention is obtained by microencapsulating an active ingredient, the active ingredient may be coated by microencapsulation with any effective nominal coating thickness. An effective nominal coating thickness will depend on the active ingredient, the coating material, the properties desired of the controlled-release formulation, and other such variables. In one embodiment, an effective nominal coating thickness is approximately 50-250 microns.

In accordance with the present invention a controlled-release active ingredient may be provided in an effective particle size. An effective particle size will generally depend on the active ingredient and the desired properties of the controlled-release formulation. In one embodiment, the active ingredient is provided in a particle size greater than about 100 microns. In one embodiment, the active ingredient is provided in a particle size smaller than about 100 microns. In one embodiment, the active ingredient is provided in a particle size smaller than about 50 microns. In one embodiment, the active ingredient is provided in a particle size smaller than about 25 microns. In one embodiment, the active ingredient is provided in a particle size smaller than about 15 microns.

Generally, although not necessarily, the particle size of the microcapsules will be in the range of a few microns up to about a thousand microns or more, with particle sizes in the approximately 30 .mu.m to 800 .mu.m preferred, and particle sizes in the range of approximately 40 .mu.m to 250 .mu.m particularly preferred.

Controlled release of active ingredients can be of particular importance in connection with the coating of substances which exert a local irritating effect on the mucosa of the gastrointestinal tract such as potassium chloride, non-steroidal antiinflammatory drugs, e.g. acetylsalicylic acid, propionic acid derivatives such as ibuprofene, lithium salts, and ferrous salts, because a prolonged period of release from multiple-units minimizes the risk of local high concentration of the active substance due to the distribution of the units and thus generally provides for lower concentrations in a particular location. In one embodiment of the present invention, controlled release of active ingredients decreases the incidence of systemic side effects. In another embodiment of the present invention, controlled release of active ingredients increases the plasma half-life of the active ingredient.

In accordance with an embodiment of the present invention, controlled release active ingredient particles or droplets are coated with a coating material. Typical coating materials may include fats, waxes, triglycerides, fatty acids, fatty alcohols, ethoxylated fatty acids and alcohols, stearates, sugars, poly(ethylene glycol), certain metals, gums, hydrocolloids, latexes, and various polymer-based formulations such as polyethylene, ethyl cellulose, ethylene-vinyl acetate, ethylene-acrylic acid, polyamides, some enteric polymers, and the like.

In addition to obtaining controlled release properties, the microencapsulation of active ingredients in accordance with the present invention provides other advantages, including decreasing the rate of degradation of active ingredients by moisture and oxidation, evaporation and sublimation. In addition, the active ingredient is protected from reacting with other ingredients, and the unpleasant taste of some active ingredients may be effectively masked.

Sustained release formulations provide for prolonged action of an active ingredient in the gastro-intestinal tract by slow release over an extended period of time. Generally, one way of achieving sustained release of a drug is to surround a core containing the active ingredient with a layer of inert material, such as an enteric substance which allows the surrounded core to pass unchanged through the stomach and disintegrate in the intestinal tract.

Those skilled in the art will appreciate that the rate at which an active ingredient will be released from a microcapsule may be modified, and will depend, inter alia, on the relative amount of capsular material to amount of active ingredient encapsulated, the chemistry of the active ingredient being encapsulated, the environment into which the microcapsule is being placed, temperature of the environment and the nature or chemical composition of the capsular material. The rate of release of active ingredient will also be determined by the relative ratios of active ingredient to capsular material, the type of capsular material, the porosity of the capsular material, the biodegradability of the capsular material, and other factors.

Generally, when an active ingredient is microencapsulated for controlled-release, it may be microencapsulated in any effective material. For example, controlled-release microcapsules may be prepared from ethylcellulose, poly-(D,L)-lactide and other polymers. See, e.g., Kawashima, Y., Lin, S. Y., Kasai, A. et al. Drug Dev. Ind. Pharm. USA 10, 467-479 (1984), Benita, S., Benoit, J. P., Puisieur, F. and Thies, C. J. Pharm. Sci. 73, 1721-1724 (1984), Bechtel, W. Radiology 161, 601-604 (1986), Tice et al., EPO 0302582, Feb. 8, 1989, all of which are hereby incorporated by reference as if fuilly set forth herein.

In one embodiment of the present invention, the active ingredient is microencapsulated with ethylcellulose. Processes for the preparation of microcapsules ensuring the controlled-release of various classes of drugs by using ethylcellulose are described, e.g., in the U.S. Pat. Nos. 3,155,590, 3,341,416, 3,488,418, 3,531,418, 3,524,910, 3,703,576, 3,891,570, 3,909,444, 3,951,851, 4,107,072, 4,389,331, 4,411,933 as well as in the published British patent application No. 2,002,318, published European patent applications Nos. 38,973 and 99,109, Wright, K. C., Wallace, S., Mosier, B., Mosier, D. J. Microencapsulation 5(1), 13-20 (1988), Wright, K. C., Charnsangavej, C., Wallace, S., Chuang, V. P., Savaraj, N. Cardiovasc. Internat. Radiol. 7, 294-298 (1984), all of which are incorporated herein by reference in their entirety as if fully set forth herein.

An active ingredient according to the present invention may be microencapsulated for controlled-release in any effective manner. For example, microcapsules may be prepared by simple or complex coacervation, interfacial cross-linking and interfacial polymerization, mechanical methods, polymer dispersion, matrix encapsulation, solvent evaporation, solvent extraction, spray drying, hot melt microencapsulation (congealing), supercritical fluid and the like.

There are many different ways to microencapsulate drugs producing sustained-release. Many of these methods can be found in "Microcapsules and Microencapsulation Techniques", 1976, M. H. Goucho, and Microcapsules and other Capsules, 1979, also by M. H. Goucho, "Aqueous Polymeric Coatings For Pharmaceutical Dosage Forms", 1989, Marcel Dekker, Inc., all of which are incorporated herein by reference. Most of the methods of producing sustained-release microparticles can be classified into either physical or chemical systems. Physical methods include such techniques as pan coating, gravity-flow, centrifuge, and the Wurster Process.

The Wurster Process employs a high velocity air stream that is directed through a cylindrical fluid bed in which the particles are suspended in the air. A coating is sprayed onto the suspended particles, and the particles flow out the top of the cylinder and descend back to the layer of fluid. The flow of air-dries the coating, so that successive layers can be applied repeatedly by further spraying. Variables that control the process include the number of cycles, temperature, pressure, and humidity, and can be used to provide the desired coating composition and thickness.

Fluid bed granulation or coating is one of the most common techniques used at the present time for small particle sustained-release. Fluidized bed equipment is available as "top spray", "bottom spray" and "tangential-spray". The core active ingredient is first preheated in the vessel to about 30° C. with hot air, placing the particles in suspension. The floating particles are then sprayed with an aqueous suspension to provide a coating, while drying at the same time. Inlet temperature, spray rate, and air throughput must be adjusted to provide optimum end product.

Chemical methods of microencapsulation include, for example, coacervation or phase separation. These techniques involves dissolving the membrane forming polymer in a suitable solvent or vehicle and the drug to be dissolved is suspended in this solution and kept under agitation The coating precipitates onto a droplet of the drug, similar to crystallization.

The coacervation method is based on salting out or phase separation from a homogeneous polymer solution of hydrophilic polymers into small droplets of a polymer-rich, second liquid phase, rather than into solid aggregates. In what is know as "simple" coacervation, an aqueous polymer solution (e.g., gelatin or carboxymethylcellulose) is partially dehydrated (or desolvated) by adding a strongly hydrophilic substance (e.g., sodium sulfate) or a water-miscible, non-solvent (e.g., ethanol, acetone, dioxane, isopropanol, or propanol), such that the water-soluble polymer is concentrated in water to form the polymer-rich phase. If water-insoluble active ingredient particles are present as a suspension or as an emulsion, the polymer-rich phase is formed on the active ingredient particle surface to form a capsule under suitable conditions. In "complex" coacervation, the polymer-rich complex (coacervate) phase is induced by interaction between two dispersed hydrophilic polymers (colloids) of opposite electric charges, with the pH of the medium being used to control the charges of the polymers.

The first polymeric material in the coacervation process is generally one that (1) is effective to microencapsulate the active ingredient upon completion of the process, (2) is substantially water-insoluble, and has appreciable solubility in the selected nonpolar organic solvent, i.e., the solubility in the selected nonpolar organic solvent is such that the phase separation-coacervation process can be carried out in that solvent, (3) provides for effective taste masking of the drug, if that is the goal desired; and (4) prevents immediate release of the microencapsulated drug in the mouth. Ethyl cellulose is generally preferred as the first polymeric material, although other polymers can be used as well, including, for example, cellulose acetate phthalate, cellulose acetate butyrate, polymethacrylates, hydroxypropyl methyl cellulose phthalate; carboxymethyl ethylcellulose; and polylactic acid and the like.

The second polymeric material in the coacervation process is generally one that is effective in assisting phase separation of the first polymeric material in the aforementioned process. Generally polyethylene may be used. However other polymers may be used as well, including, for example, polyisobutylene, ethylenevinyl acetate, and the like. Still other polymers which may serve to promote phase separation may also be used, and such polymers will be known to or may be readily deduced by those skilled in the art. The amount of second polymeric material should be selected so as to be at least minimally sufficient to promote phase separation.

Other materials may also be included in the coacervation process, including, for example, deagglomeration agents, e.g., agents effective to reduce microcapsule aggregation (e.g., colloidal silica), colorants (e.g., titanium dioxide, dyes suitable for food such as those known as F.D. & C. dyes, etc.), flavoring and/or sweetening agents, and the like.

When the active ingredient is microencapsulated by solvent evaporation and solvent extraction, an active ingredient in soluble or dispersed form is added to the polymer solution, and the mixture is emulsified in an aqueous phase containing a surface-active agent, such as poly(vinyl alcohol). Volatile organic solvents may be utilized for dissolving water-insoluble polymers, such as PLGA. Commonly used organic solvents are methylene chloride, ethyl acetate, and methyl ethyl ketone. A double emulsion process is commonly used for producing microspheres containing water-soluble active ingredients, including protein active ingredients. Both solid/oil/water (s/o/w) and water/oil/water (w/o/w) systems may be used depending on the type of active ingredient. In the solvent evaporation method, the organic solvent is evaporated by raising the temperature and/or by applying vacuum. See, for example, U.S. Pat. No. 3,523,906. In the solvent extraction method, the organic solvent diffuses into the water phase to make emulsion droplets into solid polymer microspheres. See, for example, U.S. Pat. No. 4,389,330. In both methods, the continuous phase can be non-miscible oils. The organic solvent conventionally employed in this method is a chlorinated hydrocarbon, such as methylene chloride, of which a residual amount is strictly controlled under 600 ppm to avoid known toxicities.

Hot melt microencapsulation or congealing, involves mixing a solid active ingredient or liquid active ingredient with a polymer melted at high temperatures. The active ingredient has to be stable at the polymer melting temperature. The mixture is suspended in a non-miscible solvent with continuous stirring at a temperature several degrees above the melting point of the polymer. After the emulsion is stabilized, the system is cooled until the polymer particles solidify. Interfacial polymerization involves the polymerization of monomers at the interface of two immiscible substances to form a membrane. Accordingly, for interfacial cross-linking, the polymer generally possesses finctional groups that can be cross-linked by ions or multi-functional molecules.

Spray drying may generally be accomplished by dissolving or suspending an active ingredient in a suitable (either aqueous or non-aqueous) solvent that contains dissolved polymer materials. The active ingredient can be dissolved or suspended in the solvent. Alternatively, the active ingredient solution can be emulsified in the polymer solution. The solution is atomized and microspheres are dried by a heated carrier gas. The microsphere size is controlled by the rate of spraying, the feed rate of the drug-polymer solution, the nozzle size, and temperature in the drying and cooling chambers.

In another embodiment of the present invention, an active ingredient is encapsulated for slow-release according to the process disclosed in U.S. Pat. No. 4,572,833, which is hereby incorporated by reference as if fully set forth herein.

In another embodiment of the present invention, an active ingredient is encapsulated for slow-release according to the process disclosed in U.S. Pat. No. 4,316,884, which is hereby incorporated by reference as if fully set forth herein.

In accordance with another embodiment, microparticles are microencapsulated by warming and then cooling the particles while the particles are dispersed in specific immiscible liquids, one of which is a solvent for cellulose ether when warm but not when cool. This process is generally performed using three immiscible phases:

(1) a liquid mixture of which a major part by volume is a low-viscosity liquid which acts as a solvent for the cellulose ether at warm temperatures and a minor part by volume of a polymer which acts to force the cellulose ether out of solution at cool temperature;

(2) A cellulose ether which will form a solid protective coating, is incompatible with the polymer of (1) but is soluble in the low-viscosity liquid solvent (1) at warm temperature, and which with the solvent forms a separate phase (the cellulose ether being used in an amount such that the warm solution has a viscosity of from about 4,000 to about 10,000 centipoises and may by agitation be dispersed as minute liquid entities ready to coat the active ingredient particles); and (3) micro-particles of the active ingredient, in an effective size, which are immiscible with (1) or (2) but are wettable by the warm solution of cellulose ether in the low-viscosity solvent.

The process may generally require that cellulose ethers which conform to certain specific criteria be used to prepare microencapsulated active ingredients as described. First, the cellulose ether generally must be capable, when in warm solution, of wetting the active ingredient particles so as to form a complete liquid shield around the particles which when cooled solidify without retention of the solvent. Second, the cellulose ether generally must be soluble when warmed in the low-viscosity liquid solvent, capable of forming a separate phase in the warm solvent in the presence of the polymer and insoluble in the cool solvent in the presence of the polymer. Typical of the cellulose ethers which fit the above criteria are ethyl cellulose and ethyl hydroxyethyl cellulose.

The liquid mixture used to prepare the microencapsulated active ingredient will contain two essential ingredients: (1) a major part of a low-viscosity liquid, which will act as a solvent for the cellulose ether at warm temperatures and form a separate phase containing the cellulose ether and (2) a minor part of a polymeric ingredient with which the cellulose ether is immiscible and which forces the cellulose ether out of solution at cool temperatures. Typical of the low-viscosity liquids which can be used are cyclohexane and toluene. Typical of the polymeric ingredients are polybutadiene and butyl rubber.

In another embodiment of the present invention, an active ingredient may be encapsulated according to the process disclosed in U.S. Pat. No. 5,238,714, which is hereby incorporated by reference as if fully set forth herein. Briefly, non-aggregated microcapsules having different mean diameters, including, for example, 1 .mu.m and 100 .mu.m, can be prepared by combining a polymer in a solvent with a solution of a nontoxic emulsifier and the active ingredient. The final size of the microcapsules will generally be larger the slower the stirring. For example, when the mixture is emulsified by stirring at a high speed of approximately 1500 rpms or by sonication at approximately 20 Khz and stirring at 500 rpms, microcapsules of about 1 .mu.m may be obtained. Conversely, when the mixture is emulsified by stirring at a slow speed (approximately 350 rpm), microcapsules of about 100 .mu.m may be obtained. The solution is monitored for microcapsule formation, at which point the solvent is the evaporated and the microcapsules collected after complete evaporation of the organic solvent, preferably by filtration.

Generally, an active ingredient according to the present invention may be microencapsulated for fast-release in any effective manner. For example, for active ingredients that do not dissolve in cyclohexane ethylcellulose-coated fast-release microcapsules may be prepared by mixing ethylcellulose, an anionic surface-active agent and the active ingredient to be microencapsulated together in cyclohexane at room temperature, heating the system to about 80° C. and stirring for 30 to 120 minutes in order to dissolve the ethylcellulose, cooling the system down to room temperature (20° to 30° C.) under constant stirring thereby forming a microcapsule suspension, removing the microcapsules formed by filtration and drying them. Alternatively, the anionic surface-active agent can be added after the microencapsulation, or part of the anionic surface-active agent can be added before and the other part of it is added after microencapsulation. See, e.g., U.S. Pat. No. 5,192,552, which is incorporated herein by reference in its entirety as if fully set forth herein.

In another embodiment, release of an active ingredient from the microcapsule in the mouth is limited, but rather occurs very shortly thereafter, and is virtually complete within a matter of minutes. An encapsulation to achieve this result is disclosed, for example, in U.S. Pat. No. 6,139,865, which is hereby incorporated by reference as if fully set forth herein. More specifically, the microcapsules may be prepared by first admixing the selected active ingredient, a first polymeric material to serve as the coating, and a second polymeric material to promote phase separation, in a nonpolar organic solvent. Mixing is preferably conducted along with stirring or agitation using any number of conventional means. The solvent should be one in which the polymeric materials are soluble at higher temperatures, i.e., temperatures generally on the order of 70° C. or higher, but insoluble at ambient temperature; also, the active ingredient should be substantially insoluble in the solvent at all temperatures used in the manufacturing process. After admixture of these initial components, the suspension so formed is heated for a time period and to a temperature sufficient to dissolve the first and second polymeric materials in the solvent. In addition, stirring is preferably continued at a predetermined stirring rate; a suitable stirring rate may be readily determined by one skilled in the art. The temperature is at or below the boiling point of the solvent; generally the components will be heated to a temperature of 70° or higher, and preferably to a temperature of at least about 75° C. However, care must be taken not to heat to a temperature which could degrade the drug. Cooling is then effected at a rate and to a temperature sufficient to effect phase separation of the first polymeric material and microencapsulation of the drug therein, forming a dispersion of microencapsulated drug. It will be appreciated by those skilled in the art that the cooling rate can be varied to optimize properties of the microcapsules, e.g., with respect to aggregation, flowability and release profile. The solvent and second polymeric material are then removed by decanting, filtering or the like, followed by washing with solvent to remove any traces of the second polymeric material, and then drying, again at a temperature not so high that the drug or coating material could be adversely affected. Drying is usually although not necessarily conducted for at least about 6 hours, and longer for large-scale batches, at a temperature generally in the range of approximately ambient temperature to 60° C. Drying may or may not be conducted under reduced pressure.

A variation on the aforementioned procedure provides an alternative method which may be used for heat-sensitive active ingredients. This alternative procedure involves dissolving the first and second polymeric materials in the selected nonpolar organic solvent, without addition of active ingredient, followed by heating to a temperature effective to dissolve the polymers. The active ingredient is then added, the mixture is then allowed to cool, and the remainder of the procedure described above is carried out.

In accordance with another embodiment, an active ingredient is present in a hydrogel microsphere as described in U.S. Pat. No. 5,731,005, which is hereby incorporated by reference as if fully set forth herein.

In accordance with another embodiment, an active ingredient may be microencapsulated by solvent exchange. Any effective method may be used to microencapsulate an active ingredient pursuant to the present invention by solvent exchange. For example, an active ingredient, particularly a polypeptide or protein active ingredient, may be microencapsulated as described in U.S. Pat. No. 6,599,627, which is hereby incorporated by reference as if fully set forth herein.

In accordance with another embodiment, an active ingredient may be microencapsulated with an exterior coating including a nonlamellar material such as a nonlamellar crystalline material, a nonlamellar amorphous material, or a non-lamellar semi-crystalline material. For example, an active ingredient may be microencapsulated in this manner as described in U.S. Pat. Nos. 6,638,621 and 6,989,195 which are hereby incorporated by reference as if fully set forth herein.

It will be appreciated that the effect of the active ingredient can be optimized through the use of the present invention. According to the present invention, the active ingredient may be delivered in smaller doses over a period of time rather than all at once, and the administration rate can thus be better adjusted.

In another embodiment, the present invention provides methods and compositions for the transmucosal administration of a drug to a patient in order to rapidly induce a desired systemic effect.

The micro-encapsulation of drugs and delivery of such drugs via a thin film allow for the fast dissolution while offering a convenient, compact size and discrete administration of a drug that is normally only available in a pill or capsule dosage formats.

Any effective active ingredient or medicant may be used in accordance with the present invention. An effective active ingredient or medicant in accordance with the present invention is any composition that when administered to a subject, achieves a desired physical, physiological, metabolic, pharmocologic, psychiatric, psychological, diagnostic, or the like, result. Desired results may include, for example, without limitation: diagnosing, preventing, ameliorating and/or treating a condition; maintaining or improving the well being of the subject; maintaining or improving the performance of the subject; and any other results that may be obtained by the administration of a composition to a subject. Unless otherwise required by the context, the terms active ingredient and medicant are used interchangeably and refer to the active ingredient or medicant in any form, including in a controlled release or immediate release form.

Nonlimiting examples of pharmaceutical active ingredients suitable for use herein include ace-inhibitors; acne drugs; alkaloids; amino acids; anabolic drugs; analgesics; anesthetics; angiogenesis inhibitors; antacids; antiallergenics; anti-anginaldrugs; antiarrhythmics; antiarthritics; anti-asthmatics; antibiotics; anti-cholesterolemics; anticoagulants; anti-convulsants; anti-depressants; antidiabetics; anti-diarrhea preparations; antiemetics; antiepileptics; antihistamines; anti-hypertensive drugs; anti-infectives; anti-inflammatory agents; anti-lipid agents; anti-manics; anti-nauseants; anti-stroke agents; antiobesity drugs; antiparasitics; antipsychotics; antipyretics; antispasmodic agents; antithrombotic drugs; antitumor agents; anti-tussives; anti-uricemic drugs; anti-viral agents; anxiolytic agents; appetite stimulants; appetite suppressants; awakening agents; beta blocking agents; botanical substances; bronchodilators; cardiotonics; cardiovascular agents; chelating agents; chemotherapeutic agents; cholecystokinin antagonists; cognition activators; contraceptives; coronary dilators; cough suppressants; creatine monohydrate; decongestants; dermatological agents; diabetes agents; dietary supplements; diuretics; emollients; enzymes; erectile dysfumction drugs; erythropoietic drugs; expectorants; fertility agents; ftngicides; gastro-intestinal agents; growth regulators; hemostats; hormone replacement agents; hormones; hyperglycemic agents; hypnotics; hypoglycemic agents; hypotensives; immunosuppressants; L-arginine; laxatives; L-camitine; migrain treatments; mineral supplements; mucolytics; muscle relaxants; narcotics; neuroleptics; neuromuscular blocking agents; neuromuscular drugs; non-sedating antihistamines; NSAIDS; nutritional additives; peripheral vaso-dilators; polypeptides; prostaglandins; psychoneurotropic agents; psychotropics; renin inhibitors; respiratory stimulants; salts; sedatives; selective phosphodiesterase enzyme inhibitors; sexual hormones; steroids; stimulants; sympatholytics; thyroid hormones; thyroid preparations; tranquilizers; uterine relaxants; vaso-constrictors; vasodilators; vasopressors; vertigo agents; vitamin supplements; vitamins, including for example, vitamin A, B family, C, D, E, K; wound healing agents; and the like.

Specific formulations of said ingredients may be selected by one of ordinary skill in the art depending on the specific application and other factors such as the desired effect, dosage, rate of delivery of the active ingredient, and the like.

According to an embodiment film dosage formats in accordance with the present invention provide a dissolution rate for one or more active ingredients that is comparable to that of a reference listed drug. In one embodiment, a film in accordance with the present invention is formulated such that one or more active ingredients have an effective dissolution rate when compared to a reference listed drug. The dissolution rate of a film dosage format in accordance with the present invention may be obtained in any effective manner. Generally, dissolution testing may be conducted on 12 individual dosage units for the film dosage format in accordance with the present invention and the reference drug product. The potential for pH dependence of drug release from a modified release drug product is well recognized. Accordingly, multipoint dissolution profiles generally are obtained using discriminating agitation speed and medium. A surfactant may be used under appropriate circumstances. Early sampling times of 1, 2, and 4 hours are generally included in the sampling schedule to check for premature release of the drug (dose dumping) from the formulation. See current United States Pharmacopeia (USP) 23 NF 18, sections 711 and 724, for general dissolution requirements. Generally, any effective dissolution apparatus may be used, including, for example: USP 23 Apparatus 1 (rotating basket), USP 23 Apparatus 2 (rotating paddle), USP 23 Apparatus 3 (reciprocating cylinder), USP 23 Apparatus 4 (flow-through cell), USP 23 Apparatus 7 (reciprocating disk). Generally, any effective rotation speed may be used. The speed may vary depending on the apparatus used and the test to be performed, but will generally be 50, 100, and 150 rpm (basket) 50, 75 and 100 rpm (paddle). While the dissolution test may be conducted at any effective temperature, generally the test will be conducted at the temperature of the subject for which the active is intended. For example, for humans the temperature will generally be about 37±0.5 C. The dissolution test may be conducted in any effective volume, generally the test may be conducted in about 500-1000 mL. The dissolution test may be conducted in any effective media, generally the test may be conducted in an aqueous media at various pH. The sampling schedule may be effective interval. Generally the sampling schedule may include, for example at 1, 2, and 4 hours, and every two hours thereafter until either 80% of the active ingredient is released or an asymptote is reached. Generally content uniformity testing of the film dosage format lot may be performed as described in USP 23.

In addition to application/compendial release requirements, multipoint dissolution profiles may be obtained in three other media, for example, in water, 0.1N HCl, and USP buffer media at pH 4.5, and 6.8 for a film dosage format in accordance with the present invention. The results may then be compared to a reference drug product. Sampling may be performed at any effective interval, including, for example, at 1, 2, and 4 hours and every two hours thereafter until either 80% of the drug from the drug product is released or an asymptote is reached. A surfactant may be used under appropriate circumstances.

In one embodiment, in addition to application/compendial release requirements, delayed release dissolution tests may be performed in 0.1N HCl for 2 hours (acid stage) followed by testing in USP buffer media, in the range of pH 4.5-7.5 (buffer stage) under standard (application/compendial) test conditions and two additional agitation speeds using the application/ compendial test apparatus (three additional test conditions). If the application/compendial test apparatus is the rotating basket method (Apparatus 1), a rotation speed of 50, 100, and 150 rpm may be used, and if the application/compendial test apparatus is the rotating paddle method (Apparatus 2), a rotation speed of 50, 75, and 100 rpm may be used.

Multipoint dissolution profiles are generally obtained during the buffer stage of testing. Adequate sampling may generally be performed, for example, at 15, 30, 45, 60, and 120 minutes (following the time from which the dosage form is placed in the buffer) until either 80% of the drug is released or an asymptote is reached.

Dissolution profiles may be compared using any effective method. In one embodiment, the following equation defines a similarity factor ($f_2$): $f_2 = 50 \text{ LOG} \{[1+1/n\sum_{t=1}^{n}(R_t-T_t)^2]^{-0.5} \times 100\}$ where LOG=logarithm to base 10, n=number of sampling time points, $\Sigma$=summation over all time points, $R_t$=dissolution at time point t of the reference drug product, $T_t$=dissolution at time point t of the film dosage format of the present invention.

For comparison of multipoint dissolution profiles obtained in multiple media, similarity testing should be performed using pairwise dissolution profiles (e.g., for the film dosage format of the present invention and the reference drug product) obtained in each individual medium. It is recommended that only one point past the plateau of the profiles be used in calculating the $f_2$ value. A correction for a lag time prior to similarity testing should not be performed unless justified.

Any effective $f_2$ value may be used to indicate the similarity of the dissolution profile of two dosage formats. Generally an $f_2$ value between 50 and 100 suggests the two dissolution profiles are similar. However an $f_2$ value less than 50 does not necessarily indicate lack of similarity if the value may be explained by other factors. Generally, the average difference at any dissolution sampling time point should not be greater than about 15% between the film dosage format of the present invention and the reference drug product dissolution profiles. The reference for this comparison should represent an average dissolution profile derived from an effective number of batches of the products, for example, three or more recent batches of the reference drug product.

In one embodiment of the present invention, the dissolution data obtained under the application/compendial dissolution testing conditions (media, agitation, etc.), on the film dosage format of the present invention is within the application/compendial specifications.

Dissolution profiles may also compared using other methods, including, for example, model independent or model dependent methods. See, e.g., FDA, Oral Extended (Controlled) Release Dosage Forms In Vivo Bioequivalence and In Vitro Dissolution Testing, September 1993; FDA, Guidance for Dissolution Testing of Immediate Release Solid Oral Products, 1997; FDA, Guidance for the Development, Evaluation and Application of In Vitro/In Vivo Correlations for Extended Release Solid Oral Dosage Forms, 1997; Moore, J. W. and H. H. Flanner, "Mathematical Comparison of Dissolution Profiles," Pharmaceutical Technology, 6:64-74, 1996; Skelly, J. P., et al., "Workshop Report: Scaleup of Oral Extended-Release Dosage Forms," Pharmaceutical Research, 10(12): 1800-1805, 1993, all of which are incorporated herein by reference as if fully set forth herein.

According to an embodiment film dosage formats in accordance with the present invention provide a rate and extent of absorption of one or more active ingredients that is comparable to that of a reference listed drug. Bioavailability and bioequivalence in accordance with the present invention may be obtained in ane effective manner. See, e.g., FDA Guidance for Industry Bioavailability and Bioequivalence Studies for Orally Administered Drug Products—General Considerations, which is hereby incorporated by reference as if fully set forth herein. In one embodiment, a film in accordance with the present invention is formulated such that one or more active ingredients have effective bioavailability and/or bioequivalence with a reference listed drug. In accordance with the present invention, an in vivo bioavailability and/or bioequivalence study may be performed in any effective manner. The design of a study may vary depending on the drug and dosage form. In one embodiment, the study design includes a single dose, two-treatment, two-period crossover with adequate washout period between the two phases of the study, with equal numbers of subjects being randomly assigned to each of the two dosing sequences. Generally, the number of subjects enrolled in the bioequivalence study should be determined statistically to account for the intrasubject variability and to meet the current bioequivalence interval. Generally each subject should receive the following two treatments: Treatment 1: edible film in accordance with the present invention. Treatment 2: reference listed drug. Following an overnight fast of at least 10 hours, subjects should receive either Treatments 1 or 2 above with 240 mL water. Food should not be allowed until 4 hours after dosing. Water may be allowed after the first hour. Subjects should be served standardized meals beginning at 4 hours during the study. Generally prior to and during each study phase, water may be allowed ad libitum except for 1 hour before and after drug administration. Generally the subject should be served standardized meals and beverages at specified times. Generally no alcohol or xanthine- or caffeine-containing foods and beverages should be consumed for 48 hours prior to each study period and until after the last blood sample is collected. Blood samples should generally be collected in sufficient volume for analysis of parent drug and active metabolite(s), if any. The sampling times should be such that it should be able to capture the $C_{max}$ and $T_{max}$, during the absorption period. Sampling should be carried out for at least three terminal elimination half-lives for both parent drug and active metabolite(s). Whole blood, plasma or serum, whichever is appropriate for the analytes, should be harvested promptly and samples should be frozen at −20 C. or −70 C. to maintain sample stability. The assay methodology selected should ensure specificity, accuracy, interday and intraday precision, linearity of standard curves, and adequate sensitivity, recovery, and stability of the samples under the storage and handling conditions associated with the analytical method. From the plasma drug concentration-time data, $AUC_{0-t}$, $AUC_{0-inf}$, $C_{max}$, $T_{max}$, $K_{el}$ and $t_{1/2}$ should be estimated. Analysis of variance appropriate for a crossover design on the pharmacokinetic parameters using the general linear models procedures of SAS or an equivalent program should be performed, with examination of period, sequence and treatment effects. The 90% confidence intervals for the estimates of the difference between the test and reference least squares means for the pharmacokinetic parameters ($AUC_{0-t}$, $AUC_{0-inf}$, $C_{max}$) should be calculated, using the two one-sided t-test procedure.

In another embodiment, a film dosage format of the present invention is obtained pursuant to a process including an in vitro/in vivo correlation. In one embodiment, a process for developing an in vitro/in vivo correlation is to (1) develop film dosage formats with different release rates, such as slow, medium, fast, or a single release rate if dissolution is condition independent; (2) obtain in vitro dissolution profiles and in vivo plasma concentration profiles for these film dosage formats; (3) estimate the in vivo absorption or dissolution time course using an appropriate deconvolution technique for each film dosage formats and subject (e.g., Wagner-Nelson, numerical deconvolution). These three steps establish the in vitro/in vivo correlation model. Alternative approaches to developing in vitro/in vivo correlations are possible.

Generally a correlation is estimated by a two-stage procedure including deconvolution followed by comparison of the fraction of drug absorbed to the fraction of drug dissolved. A correlation of this type is generally linear and represents a point-to-point relationship between in vitro dissolution and the in vivo input rate (e.g., the in vivo dissolution of the drug from the dosage form). In a linear correlation, the in vitro dissolution and in vivo input curves may be directly superimposable or may be made to be superimposable by the use of a scaling factor. Nonlinear correlations may also be appropriate.

In an alternative embodiment, a convolution procedure models the relationship between in vitro dissolution and plasma concentration in a single step. Plasma concentrations predicted from the model and those observed are compared directly. For these methods, a reference treatment is desirable, but the lack of one does not preclude the ability to develop an in vitro/in vivo correlation.

Generally the models should predict the entire in vivo time course from the in vitro data. In this context, the model refers to the relationship between in vitro dissolution of a controlled release film dosage form of the present invention and an in vivo response such as plasma drug concentration or amount of drug absorbed. In one embodiment, a film dosage form of the present invention is formulated by comparing the model to that of a reference drug.

The following examples are provided by way of illustration, and not limitation, of the invention.

EXAMPLE I

As noted, any desired prior art process and/or materials can be utilized to produce a film layer. The film layer may be formed, for example as follows. 3.4 g of hydropropyl cellulose and 0.4 ml of macrogol-400 (polyethylene glycol) are dissolved in 60 g of ethyl alcohol to produce a cellulose-alcohol solution. Nine milliliters of distilled water containing 90 mg of dissolved predonisolone is added to the cellulose-alcohol solution to produce a film forming composition. The film forming composition is poured into a film molding frame placed on a teflon plate. The area of teflon plate circumscribed by the frame is 9.5 square centimeters. The film forming composition is dried to form a film layer. The film layer includes an upper outer surface on top of the film layer and includes a lower outer surface on the bottom of the film layer. The lower outer surface is generally parallel to the upper outer surface. The film layer has a thickness of 40 microns.

EXAMPLE II

Sildenafil citrate, tadalafil, verdanafil, desloratadine, loratadine, loperamide (active ingredients) are microencapsulated such as to exhibit different release rates, such as slow, medium and fast, and also provided as a powder for immediate release.

EXAMPLE III

Four batches of powder matrix are prepared by individually combining the slow, medium, fast, and immediate release sildenafil with carboxymethylcellulose powder (as an adhesive), modified food starch (as a bulking agent), carrageenan (as adhesive), sucralose (intense sweetener) and talc (as flow/partitioning agent) in a fluidized bed container to form a powder matrix. Each of the four batches of powder matrix is atomized through a Nordson or similar static spray gun using compressed air onto a film layer, to produce four different batches of sildenafil film dosage formats (slow, medium, fast, and immediate release). See, for example Nordson Corporation's KINETIC (TM) spray systems (www.nordson.com). The gun creates a fine mist spray of powder particles. The gun statically electrically charges the powder particles so they adhere to the upper surface of the film layer. If desired the powder matrix can also be applied to the lower or bottom surface of the film layer. The powder matrix layer is applied such that each film dosage format will have about 25 mg sildenafil. The four batches of sildenafil film dosage format are then individually tested for dissolution, bioavailability and bioequivalence and the results are compared to the reference compound. If necessary the process is repeated with different controlled release formulations to achieve a desired result.

EXAMPLE IV

Six batches of powder matrix are prepared by combining the slow, medium, fast, and immediate release tadalafil in different ratios, including batch 1:100% immediate release; batch 2:50% immediate release 50% fast release; batch 3:50% fast release 50% medium release; batch 4:50% medium release 50% slow release; batch 5:25% immediate release 25% fast release 25% medium release 25% slow release; batch 6:33% fast release 33% medium release 34% slow release. Each of the six batches is then individually mixed with carboxymethylcellulose powder (as an adhesive), modified food starch (as a bulking agent), carrageenan (as adhesive), sucralose (intense sweetener) and talc (as flow/partitioning agent) in a fluidized bed container to form a powder matrix. Each of the six batches of powder matrix is atomized through a Nordson or similar static spray gun using compressed air onto the film layer of example I, to produce six different batches of tadalafil film dosage formats. The powder matrix layer is applied such that each film dosage format will have about 20 mg tadalafil. The six batches of tadalafil film dosage format are then individually tested for dissolution, bioavailability and bioequivalence and the results are compared to the reference compound. If necessary the process is repeated with different controlled release formulations or different ratios to achieve a desired result.

EXAMPLE V

Four batches of film are formed as in Example I except that each batch further includes one of the slow, medium, fast or immediate release loratadine of example II, such that the final concentration of loratadine is 10 mg per film dosage unit. The four batches of loratadine film dosage format are then individually tested for dissolution, bioavailability and bioequivalence and the results are compared to the reference compound. If necessary the process is repeated with different controlled release formulations or different ratios to achieve a desired result.

EXAMPLE VI

A batch of film is formed as in Example I except that it contains medium release desloratadine of example II such that the final concentration of desloratadine is 2.5 mg per film dosage unit.

Four batches of powder matrix are prepared by individually combining the slow, medium, fast, and immediate release desloratadine with carboxymethylcellulose powder (as an adhesive), modified food starch (as a bulking agent), carrageenan (as adhesive), sucralose (intense sweetener) and talc (as flow/partitioning agent) in a fluidized bed container to form a powder matrix. Each of the four batches of powder matrix is atomized through a Nordson or similar static spray gun using compressed air onto the film layer, to produce four different batches of desloratadine film dosage formats (medium/slow, medium/medium, medium/fast, and medium/immediate release (film layer/powder matrix layer)). The powder matrix layer is applied such that each film dosage format will have about 5 mg desloratadine. The four batches of desloratadine film dosage format are then individually tested for dissolution, bioavailability and bioequivalence and the results are compared to the reference compound. If necessary the process is repeated with different controlled release formulations to achieve a desired result.

While the invention is described in terms of a specific embodiment, other embodiments could readily be adapted by one skilled in the art. Accordingly, the scope of the present invention is limited only by the following claims.

The invention claimed is:

1. A composition for the oral administration of an active ingredient wherein the composition comprises an edible thin film, the film comprising a natural or synthetic water-soluble polymer, the film having a thickness of 0.01 mm -3.00 mm and exhibiting a rapid dissolution rate in the oral cavity and an active ingredient provided in controlled release formulation as a coating on said thin film, wherein the coating comprises a powder matrix comprising the active ingredient in a microencapsulated form.

2. The composition of claim 1, wherein the active ingredient is provided in a controlled-release formulation selected from the group consisting of slow-, medium-, fast- and delayed release, and a combination thereof.

3. The composition of claim 1, wherein the active ingredient is microencapsulated by a process selected from the group consisting of simple or complex coacervation, interracial cross-linking, interracial polymerization, polymer dispersion, matrix encapsulation, solvent evaporation, solvent extraction, spray drying, hot melt microencapsulation and supercritical fluid.

4. A dosage format for the oral administration of an active ingredient, the dosage format comprising:
   a) an edible thin film, the film comprising a natural or synthetic water-soluble polymer; and
   b) a multiplicity of individual microencapsulated controlled-release units each comprising the active ingredient and contained within the thin film;
   wherein the thin film is formulated and formed such that the thin film disintegrates in the oral cavity within about 15 seconds and wherein the multiplicity of individual active ingredient controlled-release units contained in the thin film are released upon said oral disintegration of the thin film, so that the active ingredient is released at a time other than immediately following oral administration.

5. The dosage format of claim 4, wherein the microencapsulated controlled-release units are encapsulated with ethyl cellulose, cellulose acetate phthalate, cellulose acetate butyrate, hydroxypropyl methyl cellulose phthalate, carboxymethyl ethyl cellulose, or carrageenan, or a mixture thereof.

6. The dosage format of claim 5, wherein the microencapsulated controlled-release units are encapsulated with ethyl cellulose, or carrageenan, or a mixture thereof.

7. The dosage format of claim 5, wherein the micro-encapsulated controlled-release units are encapsulated by a coacervation process.

8. The dosage format of claim 7, wherein a second polymeric material is used in the coacervation process, the second polymer comprising polyethylene, polyisobutylene, ethylenevinyl acetate, or a mixture thereof.

9. The dosage format of claim 5, wherein the micro-encapsulated controlled-release units are encapsulated by a solvent evaporation and solvent extraction process.

10. The dosage format of claim 5, wherein the microencapsulated controlled-release units are encapsulated by a hot melt microencapsulation process.

11. The dosage format of claim 5, wherein the microencapsulated controlled-release units have particle sizes in the range of 40 µm to 250 µm.

12. The dosage format of claim 4, further comprising a permeation enhancer.

13. The dosage format of claim 12, wherein the permeation enhancer is a bile salt, an alkylsulfate surfactant, or dimethyl sulfoxide, or any combination thereof.

14. The dosage format of claim 13, wherein the bile salt is sodium cholate, sodium glycocholate, sodium glyodeoxycholate, tautodeoxycholate, sodium deoxycholate, sodium thocholate chenocholate, hyodeoxycholate, dehydrocholate, glycochenocholate, taurochenocholate, or taurochenodexoxycholate, or any combination thereof.

15. The dosage format of claim 13, wherein the alkylsulfate surfactant is sodium dodecyl sulfate or sodium lauryl sulfate.

16. The dosage format of claim 4, further comprising an agent for adjusting pH conditions to modulate the rate of mucosal absorption of active ingredient.

17. The dosage format of claim 16, wherein the agent for adjusting pH conditions is a buffering agent.

18. The dosage format of claim 16, wherein the agent for adjusting pH conditions is contained in the film layer, in the controlled release units, or both.

19. The dosage format of claim 4, further comprising an immediate release form of the active agent, of a second active agent, or both.

20. The dosage format of claim 4, wherein the active ingredient in the controlled-release units is made available in the gastrointestinal tract.

* * * * *